United States Patent
Peters

(12) 
(10) Patent No.: US 6,451,004 B1
(45) Date of Patent: *Sep. 17, 2002

(54) METHOD FOR INTRALUMINALLY INDUCING CARDIOPLEGIC ARREST AND CATHETER FOR USE THEREIN

(76) Inventor: William S Peters, 5/70 Fletcher Street, Tamarama, New South Wales, 2026 (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/358,132

(22) Filed: Jul. 19, 1999

Related U.S. Application Data

(60) Continuation of application No. 09/085,760, filed on May 28, 1998, now Pat. No. 5,971,973, which is a division of application No. 08/879,545, filed on Jun. 20, 1997, now Pat. No. 5,762,624, which is a continuation of application No. 08/614,634, filed on Mar. 13, 1996, now abandoned, which is a division of application No. 08/427,384, filed on Apr. 24, 1995, now Pat. No. 5,752,496, which is a division of application No. 08/159,815, filed on Nov. 30, 1993, now Pat. No. 5,433,700.

(51) Int. Cl.$^7$ .............................................. A61M 31/00

(52) U.S. Cl. .................. 604/509; 604/101.01; 604/6.16

(58) Field of Search .............................. 604/6.11, 6.14, 604/28, 36, 101.01, 101.05, 8, 508, 509, 101.02, 101.03

(56) References Cited

U.S. PATENT DOCUMENTS

| | | |
|---|---|---|
| 3,769,960 A | 11/1973 | Robinson |
| 3,833,003 A | 9/1974 | Taricco |
| 4,173,981 A | 11/1979 | Mortensen et al. |

(List continued on next page.)

FOREIGN PATENT DOCUMENTS

| | | |
|---|---|---|
| EP | 0218275 | 4/1987 |
| WO | WO 91/08791 | 6/1991 |
| WO | 92/17118 | 10/1992 |

OTHER PUBLICATIONS

Cosgrove, D.M. "Management of the Calcified Aorta: An Alternative Method of Occlusion" *Ann Thorac Surg.* 36:718–719 (1983).

J.H. Foster and J.B. Threlkel "Proximal Control of Aorta with a Balloon Catheter" *Surg, Gynecology & Obstetrics* pp. 693–694 (1971).

H.G. Erath, Jr. and William S. Stoney, Jr. "Balloon Catheter Occlusion of the Ascending Aorta" *Ann Thorac Surg.* 35:560–561 (1983).

Buckberg, G.D., "Strategies and Logic of Cardiplegic Delivery to prevent, Avoid, and Reverse Ischemic and Reperfusion Damage" *J Thorac Cardio Vasc Surg*, 1987, 93:127–129.

Yamaguchi, A., "A Case of a Reoperation Using a Balloon Catheter with Blocked Pars Ascendes Aortae" *Kyobu Geka*, Oct. 1991, 42(11):961–964.

Rossi, F., "Long–Term Cardiopulmonary Bypass by Peripheral Cannulation in a Model of Total Heart Failure" *J Thorac Cardio Vasc Surg*, 1990, 100:914–921.

(List continued on next page.)

*Primary Examiner*—Anhtuan T. Nguyen

(57) ABSTRACT

A process for inducing cardioplegic arrest of a heart in situ in a patient's body, comprising maintaining the patient's systemic circulation by peripheral cardiopulmonary by-pass, occluding the ascending aorta through a percutaneously placed arterial balloon catheter, venting the left side of the heart, and introducing a cardioplegic agent into the coronary circulation. This procedure readies the heart for a variety of surgical procedures that can be performed percutaneously through lumina in the catheter. An aortic catheter for use in the process is also described.

6 Claims, 6 Drawing Sheets

U.S. PATENT DOCUMENTS

| | | |
|---|---|---|
| 4,248,224 A | 2/1981 | Jones |
| 4,276,874 A | 7/1981 | Wolvek et al. |
| 4,527,549 A | 7/1985 | Gabbay |
| 4,531,936 A | 7/1985 | Gordon |
| 4,540,399 A | 9/1985 | Litzie et al. |
| 4,592,340 A | 6/1986 | Boyles |
| 4,601,713 A | 7/1986 | Fuqua |
| 4,655,746 A | 4/1987 | Daniels et al. |
| 4,664,125 A | 5/1987 | Pinto |
| 4,680,029 A | 7/1987 | Ranford et al. |
| 4,697,574 A | 10/1987 | Karcher et al. |
| 4,705,507 A | 11/1987 | Boyles |
| 4,741,328 A | 5/1988 | Gabbay |
| 4,785,795 A | 11/1988 | Singh |
| 4,804,365 A | 2/1989 | Litzie et al. |
| 4,877,035 A | 10/1989 | Bogen et al. |
| 4,889,137 A | 12/1989 | Kolobow |
| 4,902,272 A | 2/1990 | Milder et al. |
| 4,902,273 A | 2/1990 | Choy et al. |
| 4,943,275 A | 7/1990 | Stricker |
| 4,990,139 A | 2/1991 | Jang |
| 5,011,469 A * | 4/1991 | Buckberg et al. ......... 604/6.11 |
| 5,059,178 A | 10/1991 | Ya |
| 5,116,305 A | 5/1992 | Milder et al. |
| 5,163,906 A | 11/1992 | Ahmadi |
| 5,167,628 A | 12/1992 | Boyles |
| 5,171,232 A | 12/1992 | Castillo et al. |
| 5,176,619 A | 1/1993 | Segalowitz |
| 5,176,628 A | 1/1993 | Charles et al. |
| 5,186,713 A | 2/1993 | Raible |
| 5,195,942 A | 3/1993 | Weil et al. |
| 5,209,723 A | 5/1993 | Twardowski et al. |
| 5,219,326 A | 6/1993 | Hattler |
| 5,254,097 A | 10/1993 | Schock et al. |
| 5,306,249 A | 4/1994 | Don Michel |
| 5,308,320 A | 5/1994 | Safar |
| 5,312,344 A * | 5/1994 | Grinfeld et al. ....... 604/101.05 |
| 5,425,705 A * | 6/1995 | Evard et al. ............ 604/508 X |
| 5,433,700 A * | 7/1995 | Peters ...................... 604/6.14 |
| 5,451,207 A | 9/1995 | Yock |
| 5,460,610 A | 10/1995 | Don Michel |
| 5,478,309 A | 12/1995 | Sweezer et al. |
| 5,499,996 A | 3/1996 | Hill |
| 5,562,606 A | 10/1996 | Huybregts |

OTHER PUBLICATIONS

Sabiston, D.C., Textbook of Surgery, 10th Ed., 1972, pp. 2021–2023, 2114–2121.

Uchida et al., "Percutaneous Cardiomyotomy and Valvulotomy with Angioscopic Guidance" American Heart Journal, 1991, 121(4, part 1):1221–1224.

Uchida et al., "Percutaneous Fiberoptic Angioscopy of the Cardiac Valves" American Heart Journal, 1991, 121(6, part 1):1791–98.

"Occlusion Balloon Catheters: Instructions for Use" Medi–Tech, Boston Scientific Corporation, Rev. 3/91.

Okita et al. "Utilization of Triple–Lumen Balloon Catheter for Occlusion of the Ascending Aorta During Distal Aortic Arch Surgery with Hypothermic Retrograde Cerebral Circulation Technique Through Left Thoracotomy." J Card Surg., 10:699–702 (1995).

Partington, M. T. "Studies of retrograde cardioplegia: IL Advantages of antegrade/retrograde cardioplegia to optimize distribution in jeopardized myocardium", J. Throac Cardiovasc Surgery, 1989, 97(4):613–622.

Textbook of Surgery, 10th ed. (W. B. Saunders Co., Philadelphia, 1972) pp. 2021–2023, 2114–2121.

Ishizaka, M. "Myocardial protection by retrograde cardiac perfusion with cold modified krebs solution through coronary sinus during complete ischemic arrest for 120", Ass. Thorac Surg (Japan) 25(12):1592–1601 (1977).

Takashashi, M. "Retrograde coronary sinus perfusion for mycardial protection in aortic valve surgery", Jpn Assoc Thorac Surg. 30(3):306–318 (1982).

Gundry et al. "A comparison of retrograde cardiolegia versus antegrad cardioplegia in the presence of coronary artery obstruction" Ann Thorac Surg. 38(2):124–127(1984).

Lust et al. "Improved protection of chronically inflow–limited myocardium with retrograde coronary sinus cardioplegia", Circulation 78(5pt2)III217–223 (1988).

Crooke et al. "Biventricular Distribution of cold blood cardioplegic solution administered by different retrograde techniques", J. Thorac Cardiovasc Surg. 10240:631–636 (1991).

Razi, "The challenge of cacific aortitis", J. Card surg 8:102–107 (1993).

Ogawa et al. "Aortic arch reconstruction without aortic cross–clamping using separate extra corporal circulation", J. Jpn Assoc Thorac Surg. 41(11):2185–2190 (1993).

Erah, Jr. and Stoney, Jr. "Balloon catheter occlusion of the ascending aorta" Ann Thorac Surg. 35:560–561 (1983).

* cited by examiner

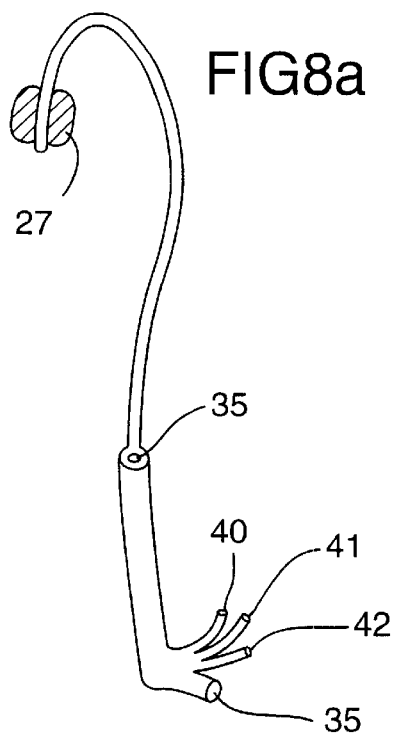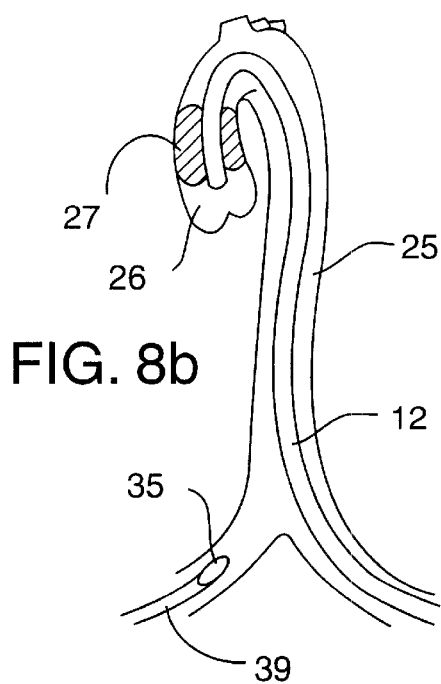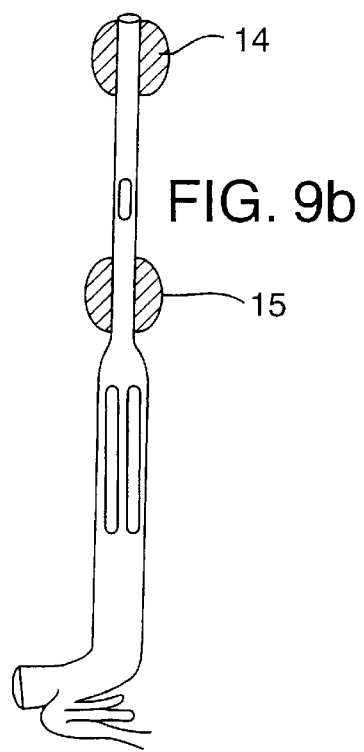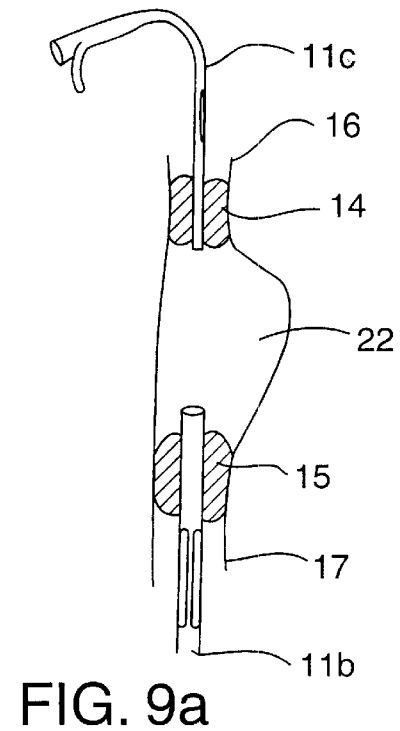

METHOD FOR INTRALUMINALLY INDUCING CARDIOPLEGIC ARREST AND CATHETER FOR USE THEREIN

CROSS REFERENCE TO RELATED APPLICATIONS

This application is a continuation of application Ser. No. 09/085,760, filed May 28, 1998 now U.S. Pat. No. 5,971,973, which is a divisional of application Ser. No. 08/879,545 filed Jun. 20, 1997, now issued as U.S. Pat. No. 5,762,624, which is a continuation of application Ser. No. 08/614,634 filed Mar. 13, 1996, now abandoned, which is a divisional of application Ser. No. 08/427,384 filed Apr. 24, 1995, now issued as U.S. Pat. No. 5,752,496, which is a divisional of application Ser. No. 08/159,815 filed Nov. 30, 1993, now U.S. Pat. No. 5,433,700, now reissued as U.S. Pat. No. RE35352. The complete disclosures of all of these applications are hereby incorporated herein by reference for all purposes.

FIELD OF THE INVENTION

The present invention relates to a method for inducing cardioplegic arrest in a heart and to catheters for use in that method.

BACKGROUND OF THE INVENTION

The use of extracorporeal cardiopulmonary by-pass for cardiac support has become well established. This use has, however, involved median sternotomy or less commonly thoracotomy with all of the trauma that necessarily accompanies such a major surgical procedure.

The present invention contemplates, at least in its preferred embodiments, the possibility of effective ascending aortic occlusion, cardioplegia, venting, right heart deflation and topical cooling in association with extracorporeal cardiopulmonary by-pass all without necessitating a median sternotomy or other thoracic incision.

DISCLOSURE OF THE INVENTION

In a first aspect the present invention consists in a method for inducing cardioplegic arrest of a heart in situ in a patient's body, comprising the steps of:
(a) maintaining systemic circulation with peripheral cardiopulmonary by-pass;
(b) occluding the ascending aorta through a percutaneously placed arterial balloon catheter;
(c) introducing a cardioplegic agent into the coronary circulation; and
(d) venting the left side of the heart.

The method according to the present invention may be carried out on humans or other mammalian animals. The method is of particular applicability in humans as it allows an alternative approach to open heart surgery and the development of closed cardioscopic surgery. The method according to the invention enables a percutaneous by-pass system to be associated with cardioplegia, venting and cooling of the heart which subverts the need for median sternotomy. This may, in turn, reduce the complications of the surgery.

The maintenance of the systemic circulation involves establishing a cardiopulmonary by-pass. The blood may be drawn into the by-pass merely by positioning a percutaneous catheter into the right atrium and/or into one or both of the vena cavae through which venous blood may be drawn from the heart into an extracorporeal pump oxygenator. In more preferred embodiments of the invention a single catheter with two inflatable cuffs, or two separate catheters, each with an inflatable cuff are introduced into the vena cavae to occlude them adjacent to their right atrial inlets. This allows isolation of the right atrium and allows blood to be drawn from the vena cavae into the by-pass system. There is also preferably provision for percutaneous communication via one catheter with the right atrium to allow infusion of saline into the right atrium. This infusion has the advantage that it allows the heart to be cooled and improves visual acuity within the right heart allowing direct cardioscopic examination and/or intervention.

The catheter used to decompress the right atrium and to draw blood into the by-pass is preferably introduced through the femoral vein by percutaneous puncture or direct cut down. If other than simple venous drainage is required catheters with inflatable cuffs, as described above, are placed preferably such that in inflatable cuff of the cannula is positioned within each of the inferior (suprahepatic) and superior vena cavae. There is preferably a lumen in the cannula acting as a common blood outlet from the vena cavae leading to the pump oxygenator. A separate lumen is preferably used to infuse saline between the two inflated cuffs into the right atrium. If, alternatively, separate catheters are used to occlude each of the inferior and superior vena cavae than the cannula for the inferior vena cavae is preferably introduced percutaneously from the femoral vein and that for the superior vena cavae is introduced percutaneously through the jugular or subclavian vein.

The ascending aorta is preferably occluded by a balloon catheter introduced percutaneously through the femoral artery. This catheter must carry adjacent its tip an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon is of a cylindrical shape to fully and evenly accommodate the lumen of the ascending aorta. This maximizes the surface area contact with the aorta, and allows for even distribution of occlusive pressure.

The balloon of the catheter is preferably inflated with a saline solution to avoid the possibility of introducing into the patient an air embolism in the event that the balloon ruptured. The balloon should be inflated to a pressure sufficient to prevent regurgitation of blood into the aortic root and to prevent migration of the balloon into the root whilst not being so high as to cause damage or dilation to the aortic wall. An intermediate pressure of the order of 350 mmHg has been proven effective in trials.

The aortic catheter is preferably introduced under fluoroscopic guidance over a suitable guidewire. Transoesophageal echocardiography can alternatively be used for positioning as has been described with reference to the venous catheter. The catheter may serve a number of separate functions and the number of lumina in the catheter will depend upon how many of those functions the catheter is to serve. The catheter can be used to introduce the cardioplegic agent, normally in solution, into the aortic root via one lumen. The luminal diameter will preferably be such that a flow of the order of 250–500 ml/min of cardioplegic solution can be introduced into the aortic root under positive pressure to perfuse adequately the heart by way of the coronary arteries. The same lumen can, by applying negative pressure to the lumen from an outside source, effectively vent the left heart of blood or other solutions. It may also be desirable to introduce medical instruments and/or a cardioscope into the heart through another lumen in the catheter. The lumen should be of a diameter suitable to pass a fibre-optic light camera of no greater than 3 mm diameter. It is however, preferable that the diameter and cross-sectional design of the internal lumina is such that the external diameter of the catheter in its entirety is small enough to allow its introduction into the adult femoral artery by either percutaneous puncture or direct cut-down The oxygenated blood returning to the body from the by-pass system may be conveyed into the aorta from another lumen in the cannula carrying the balloon. In this case the returning blood is preferably discarded from the catheter in the external iliac artery. In another embodiment of the invention, and in order to reduce the diameter of the catheter carrying the balloon, a separate arterial catheter of known type may be used to return blood to the patient from the by-pass system. In this case a short catheter is positioned in the other femoral artery to provide systemic arterial blood from the by-pass system. The control end of the catheter, i.e. that end that remains outside of the body, should have separate ports of attachment for the lumina. The catheter length should be approximately 900 mm for use in humans.

The cardioplegic agent may be any of the known materials previously known to be useful, or in the future found to be useful, as cardioplegic agents. The agent is preferably infused as a solution into the aortic root through one of the lumina of the aortic catheter.

In another aspect the present invention consists in a catheter for use in occluding the ascending aorta comprising an elongate tube having one or more continuous lumina along its length, an inflatable cuff is disposed about the tube adjacent one end thereof, the cuff being of such a size that upon being inflated it is able to occlude the ascending aorta of a patient.

The catheter and method according to the present invention can be used to induce cardioplegic arrest and may be used in a number of surgical procedures. These include the following:

1. Coronary artery revascularization such as:
    (a) angioscopic laser introduction or angioscopic balloon angioplasty catheter into the coronary arteries via one lumen of the aortic catheter; or
    (b) thoraco dissection of one or both of the mammary arteries with revascularization achieved by distal anastomoses of the internal mammary arteries to coronary arteries via a small left anterior thoracotomy.
2. Secundum-type atrial septal defect repair such as by:
    (a) "Closed" cardioscopic closure, or
    (b) Closure as an "open" procedure via a mini-right thoracotomy.
3. Sinus venosus defect repairs similar to 2 above.
4. Infundibular stenosis relief by cardioscopic techniques.
5. Pulmonary valvular stenosis relief by cardioscopic techniques.
6. Mitral valve surgery via a small right thoracotomy.
7. Aortic stenosis relief by the introduction of instrumentation via a lumen in the aortic catheter into the aortic root.
8. Left ventricular aneurysm repair via a small left anterior thoracotomy.

BRIEF DESCRIPTION OF THE DRAWINGS

Hereinafter given by way of example are preferred embodiments of the present invention described with reference to the accompanying drawings in which:

FIGS. 8a and 8b show schematically two alternative arrangements to the catheter shown in FIG. 4;

FIGS. 9a and 9b show schematically two alternative catheter arrangements for the isolation of the right atrium and venous drainage.

BEST METHOD OF CARRYING OUT THE INVENTION

Figure 1:
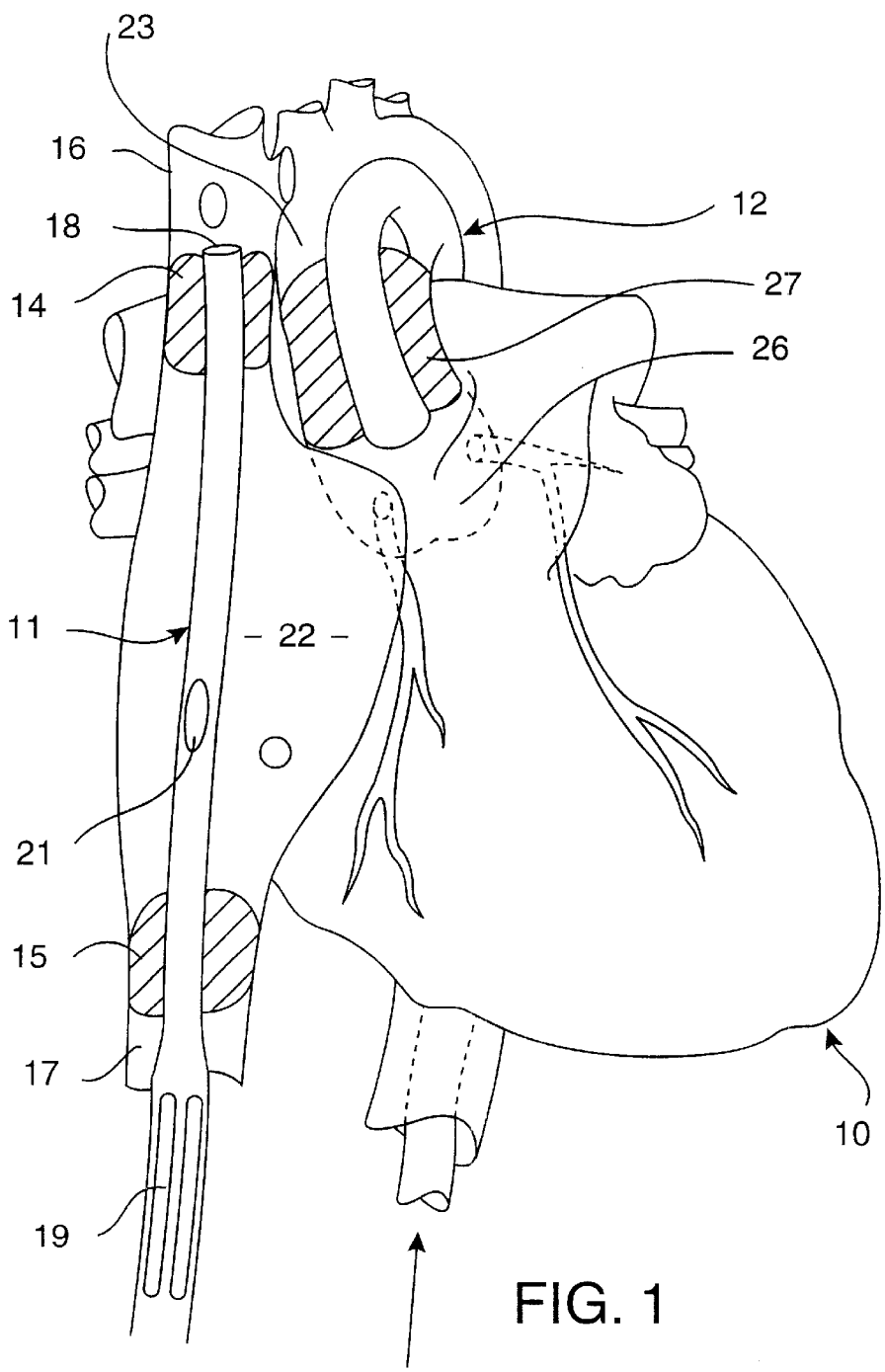
FIG. 1 is a schematic partly cut-away representation of a patient's heart having percutaneous catheters placed therein for carrying out the method according to the present invention.
Figure 2:
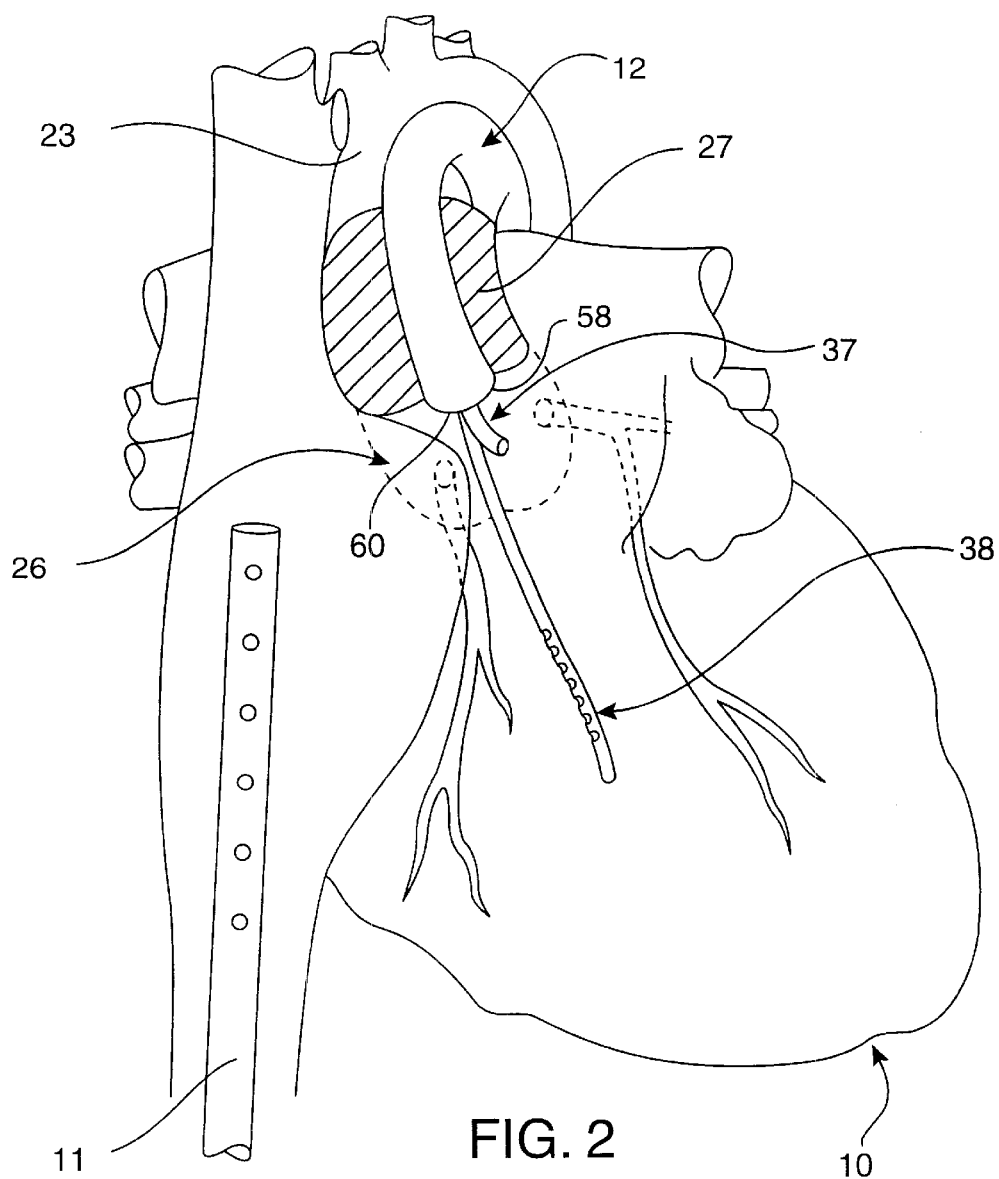
FIG. 2 is a similar view to FIG. 1 showing the aortic catheter in position but including an angioscope and a left ventricular venting cannula introduced into the aortic root and left ventricle respectively, via separate lumina within the aortic catheter.

The heart 10 of FIGS. 1 and 2 is positioned in the living body of a patient and is accessed percutaneously.

In order to induce cardioplegia in the heart while maintaining the patient it is necessary to divert the patient's blood circulation through an extracorporeal cardiopulmonary by-pass system. This is achieved by isolating the heart 10 on both the venous and arterial sides using appropriate percutaneously inserted venous catheter 11, aortic balloon catheter 12, and if this catheter 12 doesn't have provision for arterial blood return, arterial catheter 39 (see FIG. 3). The venous outflow and arterial inflow lumina of the catheters 11 and 12 of the by-pass system are of sufficient cross sectional area to achieve standard blood flows to maintain the patient's systemic circulation during the period of extracorporeal circulation.

In the case of the use of a single venous double-ballooned catheter 11, as is shown in FIG. 1, the catheter 11 is inserted through the femoral vein preferably. A suitable guide wire is initially inserted and the catheter 11 is then introduced in known manner under fluoroscopic guidance. The catheter 11 includes a pair of separately inflatable balloons 14 and 15 each connected to a balloon inflation control device (not shown) through suitable lumina in the catheter 11. The balloon 14 is adapted to occlude the superior vena cavae 16 while the balloon 15 is adapted to occlude the suprahepatic inferior vena cavae 17. A blood withdrawal lumen in the catheter 11 has an inlet orifice 18 flush with the balloon 14, to avoid venous collapse during blood flow into the catheter 11, and a series of inlet slots 19 in the inferior vena cavae. Blood drawn into the inlets 18 and 19 enters a common single lumen. Blood drawn into the by-pass system through the catheter 11 is oxygenated and returned to the patient in a manner which will be hereinafter described.

A separate lumen in the catheter 11 opens into the right atrium 22 through aperture 21 to allow evacuation of blood from the right heart and the infusion of saline to induce topical cooling and/or to improve visual acuity within the right heart.

In use, after the catheter 11 has been positioned the balloons may be inflated or deflated to vary the rate of venous return to the right atrium 22 and therefore the degree of decompression of the left heart. Venous drainage may be effected by gravitational drainage or by applying a degree of negative pressure to assist flow into the pump oxygenator. It will be appreciated that the distance between the balloons 14 and 15 will need to be correct for a given patient and this may be assessed by X-ray examination to allow selection of an appropriately sized catheter. Alternatively separate catheters 11b and 11c could be used, as is shown in FIG. 9a, for the inferior and superior vena cavae. The cannula 11b being introduced as has been described above and the cannula 11c being introduced through the jugular or subclavian vein. It will also be appreciated that for simple operations not requiring complete occlusion of the right atrium it is possible to merely insert a simple catheter 11 into the right atrium to draw blood into the by-pass system as is seen in FIG. 2. Positioning under fluoroscopic guidance is not essential in this case.

Figure 3:
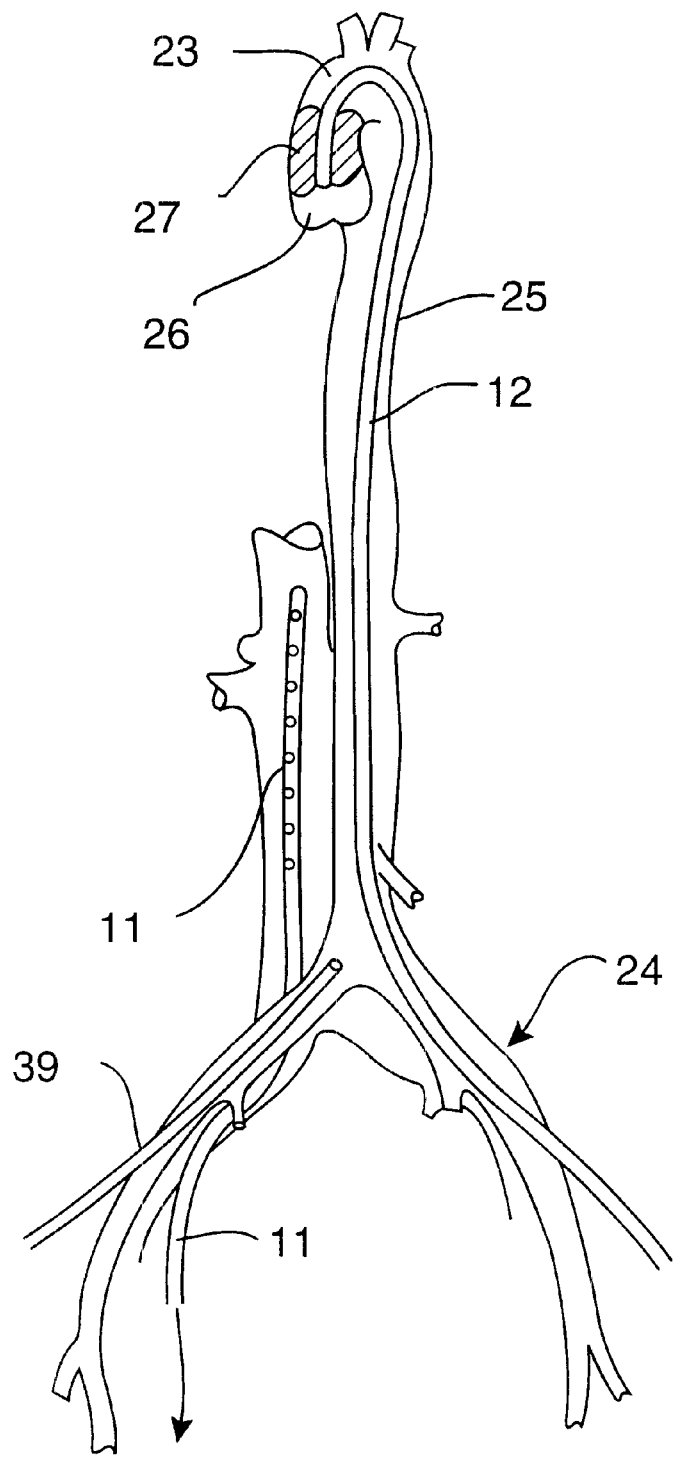
FIG. 3 is a front elevational view of part of the vascular system of a patient showing, inter alia, the aortic balloon catheter positioned in the ascending aorta via the femoral artery.
Figure 4:
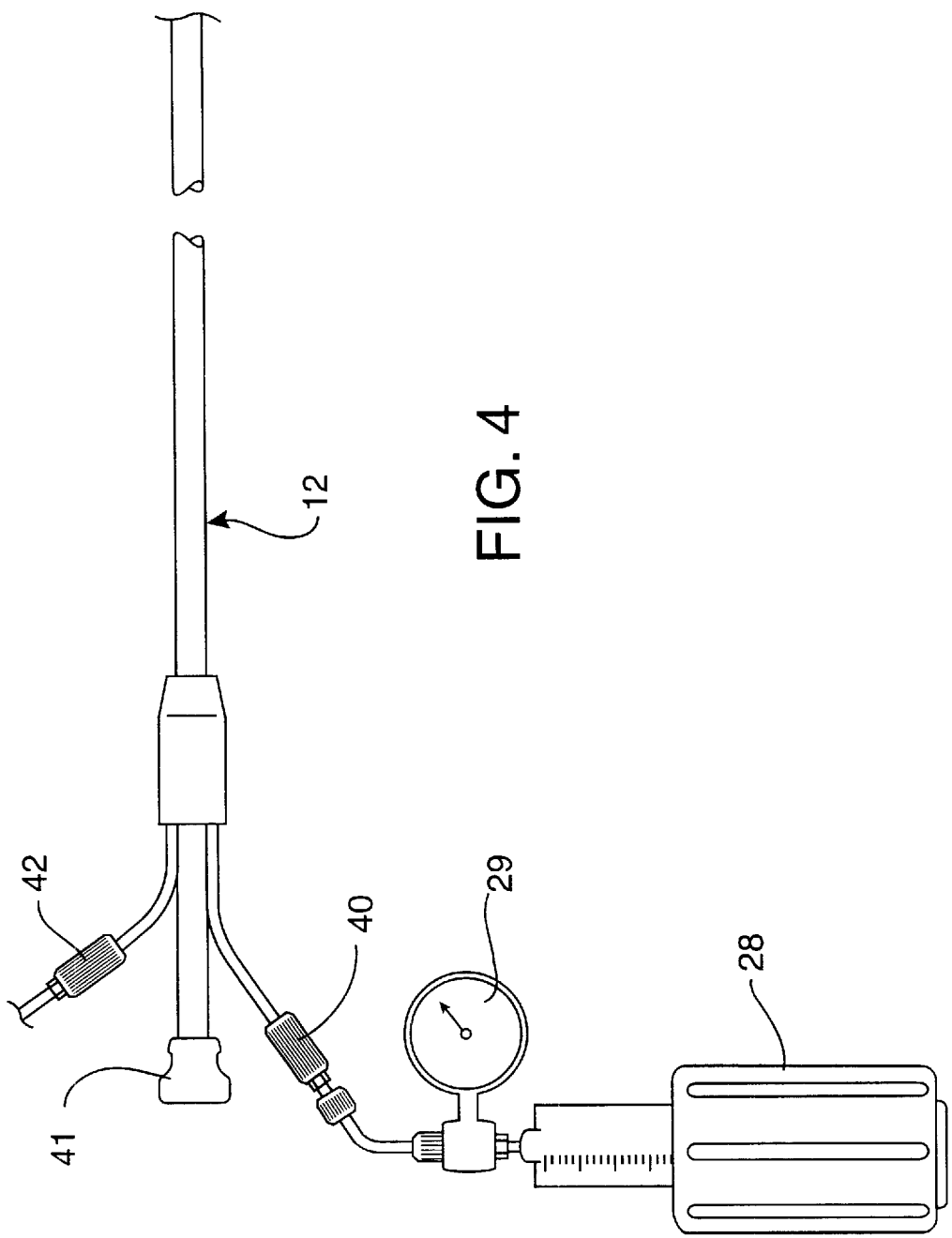
FIG. 4 is a side elevational view of the control end of the aortic catheter according to the present invention.

The catheter 12 is positioned in the manner described above with its free end located in the ascending aorta 23. The catheter 12 is so positioned by insertion preferably through the femoral artery 24 and via the descending aorta 25 as is seen in FIG. 3.

If desired a fluoroscopic dye may be introduced into the aortic root 26 through the catheter 12 for accurate positioning of the tip of the catheter 12 relative to the aortic root 26 and the coronary ostia.

The catheter 12 carries at its free end a balloon 27. The balloon 27 is arranged to be inflated with saline from an inflation control device 28 of known type through a lumen in the catheter 12. The device 28 is fitted with a pressure gauge 29 to allow the operator to control the inflation of the balloon 27. The pressure of the fully inflated balloon 27 should be of the order of 350 mmHg so as to be sufficient to effectively occlude the aorta and to prevent the balloon moving while not being so great as to cause damage to the aortic wall. The balloon 27 should have a maximum diameter sufficient to occlude the aorta and for this purpose the maximum diameter should be about 35 mm. The balloon 27 should have a length of about 40 mm so as not to be so long as to occlude or impede blood flow to the coronary arteries or to the brachiocephalic, subclavian or carotid arteries. If necessary in any given patient the required length and diameter of the balloon may be determined by angiographic, X-ray examination or echocardiography and an appropriately sized catheter selected on that basis.

Figure 5:
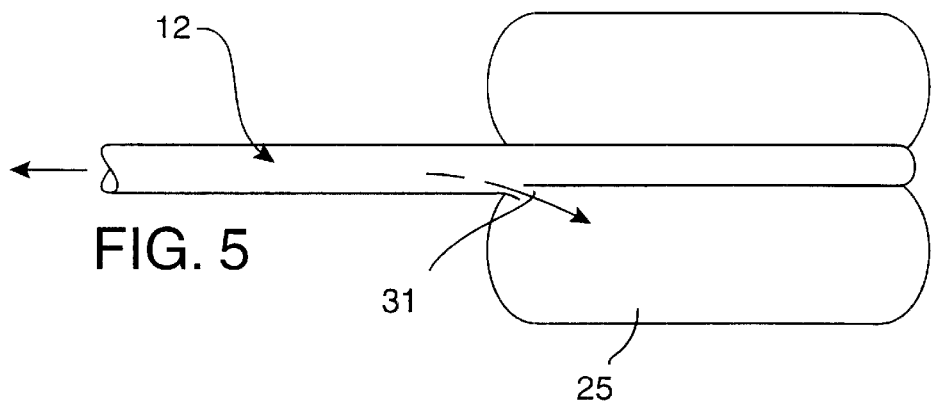
FIG. 5 is a partly cut away side elevational view of the balloon end of the catheter of FIG. 4 in an inflated condition.

The balloon 27 is preferably connected to the lumen 32 through which it is inflated at the end of the balloon 27 distal to the tip of the catheter 12 through orifice 31 (see FIG. 5). This allows the tip of the catheter to contain fewer lumina than the remainder of the catheter. Accommodation of the deflated balloon around the tip of the catheter is thus possible without adding to the diameter of the tip as compared with the rest of the catheter 12.

Figures 6A, 7:
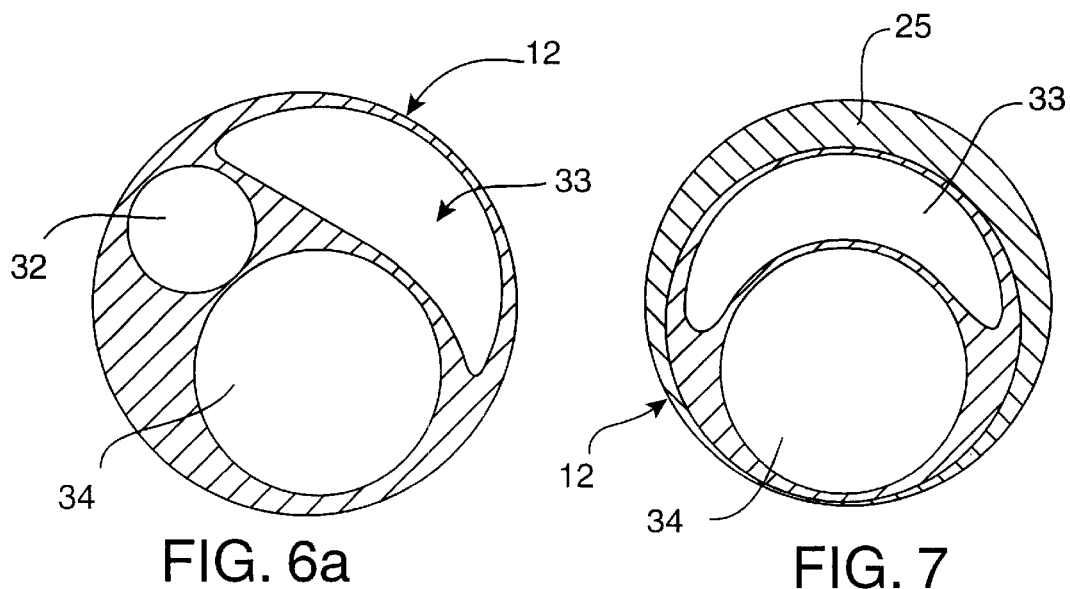
FIG. 6a is a cross-sectional view of the catheter of FIG. 4 intermediate the control end and the balloon end.
FIG. 7 is a cross-sectional view through the balloon end of the catheter of FIG. 4.
Figure 6B:
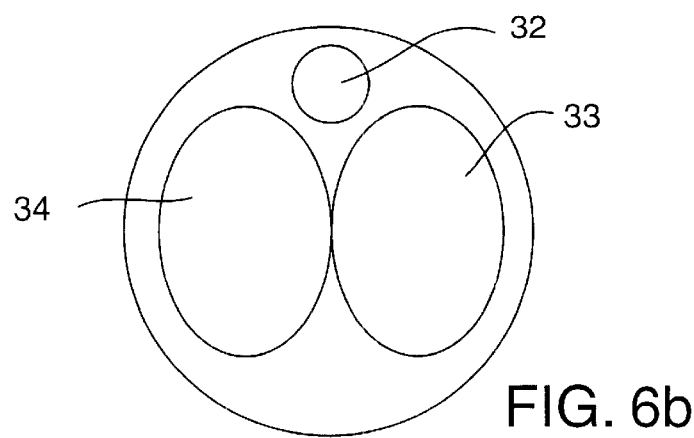
FIG. 6b is an alternative cross-sectional arrangement of the lumina in the catheter of FIG. 4.

The catheter 12 includes a plurality of lumina (see FIGS. 6 and 7). In addition to the balloon inflation lumen 32 there is at least a single venting/cardioplegia lumen 33 of circular cross-section. There may be a separate and extra circular lumen 34 for instrumentation. If two lumens are present the venting/cardioplegia lumen may be circular or crescent shaped in cross-section (FIGS. 6a, 6b). The diameter of the various lumina should be as small as practicable commensurate with the intended use. In addition, there may be a continuous lumen 35 through which arterial blood is returned from the by-pass. This may flow out of the catheter 12 through an orifice in the region of the external iliac artery. In alternative embodiments of the invention such as shown in FIGS. 3 and 8 the arterial return lumen 35 may comprise its own catheter 39 of known type introduced into the other femoral artery or some other suitable artery.

In use the catheter 12 is introduced percutaneously by puncture or cutdown as has been described and once blood flow through the by-pass is established (including systemic cooling) flows are reduced and the balloon 25 is inflated. Flows are then returned to the operating levels and a suitable cardioplegic agent is introduced into the aortic root. Once the full volume of cardioplegic agent has been given and cardiac arrest achieved, the lumen is then used to vent the heart. The heart may then be operated on or examined by insertion of instrumentation 37 such as a cardioscope or a laser into the heart through the lumen 34 or through atrial trocars. Alternatively, with the heart on by-pass as described above the heart can be approached by an open method by an incision other than median sternotomy. Venting of the left ventricle may be effected by providing an extended cannula 38 projecting from lumen 33 into the left ventricle (see FIG. 2) or by simply applying negative pressure to the venting lumen 33 of the aortic catheter. To reverse cardioplegic arrest the body is rewarmed and the balloon 27 deflated. Aortic blood is thus allowed to perfuse the heart. Whilst the body remains supported by peripheral cardiopulmonary by-pass, the return of the heart rhythm is awaited. External defibrillation my be necessary. Weaning from by-pass is then completed in a routine fashion.

What is claimed is:

1. A method for inducing cardioplegic arrest of a heart in situ in a patient's body, comprising the steps of:

(a) maintaining systemic circulation with peripheral cardiopulmonary by-pass that includes a percutaneous catheter introduced into the right atrium and/or into one or both of the vena cavae to draw venous blood into the cardiopulmonary by-pass, in which the percutaneous catheter has two inflatable cuffs, each cuff being adapted to occlude one of the vena cavae and the percutaneous catheter having a lumen or lumanae to draw venous blood from each of the vena cavae into the cardiopulmonary by-pass;

(b) occluding the ascending aorta through a percutaneously placed arterial balloon catheter;

(c) introducing a cardioplegic agent into the coronary circulation; and (d) venting the left side of the heart.

2. A method as claimed in claim 1, in which the ascending aorta is occluded by a balloon catheter percutaneously placed through one of the femoral arteries.

3. A method as claimed in claim 2 in which the catheter has a lumen or lumina through which the cardioplegic agent or medical instruments and/or a cardioscope may be introduced into the heart and/or through which the left side of the heart is vented.

4. A method as claimed in claim 1 in which saline is introduced into the right atrium through a lumen in the percutaneous catheter which opens between the two cuffs.

5. A method as claimed in claim 1 in which the percutaneous catheter is introduced into the heart through the femoral vein.

6. A method as claimed in claim 1 in which the systemic circulation is maintained through a cardiopulmonary by-pass that includes an oxygenated blood return catheter introduced into one of the femoral arteries.

* * * * *